United States Patent [19]

Blacklock et al.

[11] Patent Number: 5,157,129
[45] Date of Patent: Oct. 20, 1992

[54] ENANTIOSPECIFIC SYNTHESIS OF S-(+)-5,6-DIHYDRO-4-(R-AMINO)-4H-THIENO(2,3-B)THIOPYRAN-2-SULFONAMIDE-7,7-DIOXIDE

[75] Inventors: Thomas J. Blacklock, Clark; Todd K. Jones, Edison; Edward J. J. Grabowski, Westfield; David J. Mathre; Julie J. Mohan, both of Edison; Paul Sohar, Warren; F. Edward Roberts, Princeton; Lyndon C. Xavier, Edison, all of N.J.

[73] Assignee: Merck & Co., Inc., Rahway, N.J.

[21] Appl. No.: 510,804

[22] Filed: Apr. 18, 1990

[51] Int. Cl.$^5$ .............................. C07D 495/04
[52] U.S. Cl. .................................... 549/23
[58] Field of Search ........................... 549/23

[56] References Cited

U.S. PATENT DOCUMENTS

| | | | |
|---|---|---|---|
| 4,677,115 | 6/1987 | Baldwin et al. | 514/431 |
| 4,797,413 | 1/1989 | Baldwin et al. | 544/357 |
| 4,946,859 | 8/1990 | Hoffman, Jr. et al. | 549/23 |

OTHER PUBLICATIONS

Morrison & Boyd, 3rd Ed. "Organic Chemistry", p. 630, Reduction to Alcohols.
Morrison & Boyd, 3rd Ed. "Organic Chemistry", p. 737, Conversion of $RCH_2OH$ into $RCH_2NH_2$.
Merck Index, 10th Ed. p. ONR-96, "Williamson Synthesis".
Corey et al., *J. Amer Chem Soc.*, 1987, 109, 7925–7926.
Corey et al., *J. Amer Chem Soc.*, 1987, 109, 5551–5553.
Corey et al., *J. Org Chem.*, 1988, 53, 2861–2863.
Corey et al., *Tet. Letters*, 1989, 30, 5547–5550.
Corey et al., *Tet. Letters*, 1989, 30, 6275–6278.
Corey et al., *Tet. Letters*, 1990, 31, 611–614.
Youn et al., *Tet. Letters*, 1988, 29, 4453–4456.
Itsuno et al., *J. Chem Soc.*, Perk. Trans. 1984, 1, 2887.
Itsuno et al., *J. Chem Soc.*, Chem. Commun. 1983, 469.
Corey et al., *Tet. Letters*, 1990, 31, 601–604.
Itsuno et al., *J. Org Chem.*, 1984, 49, 555–557.
Itsuno et al., *Bull Chem Soc Japan*, 1987, 60, 395–397.

*Primary Examiner*—C. Warren Ivy
*Assistant Examiner*—Catherine S. Kilby Scalzo

[57] ABSTRACT

5,6-Dihydro-4-(R-amino)-4H-thieno[2,3-b]-thiopyran-2-sulfonamide-7,7-dioxide is a potent carbonic anhydrase inhibitor useful in the treatment of ocular hypertension and glaucoma. The S-(+)-enantiomer of that compound, the more active enantiomer, is prepared by a process involving an intermediate step of an enantioselective reduction of a carbonyl group employing an oxazaborolidine chiral catalyst.

28 Claims, No Drawings

ENANTIOSPECIFIC SYNTHESIS OF S-(+)-5,6-DIHYDRO-4-(R-AMINO)-4H-THIENO(2,3-B)THIOPYRAN-2-SULFONAMIDE-7,7-DIOXIDE

SUMMARY OF THE INVENTION

This invention is concerned with a process for the enantioselective synthesis of S-(+)-5,6-dihydro-4-(R-amino)-6-$R^1$-4H-thieno[2,3-b]-thiopyran-2-sulfonamide-7,7-dioxide of formula I:

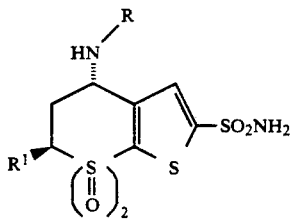

Compounds represented by this structure are powerful carbonic anhydrase inhibitors useful in the treatment of ocular hypertension and glaucoma associated therewith.

The enantioselectivity is achieved at an intermediate step in the synthesis which involves the reduction of a carbonyl group to a secondary alcohol in the presence of an oxazaborolidine chiral catalyst of structure II

BACKGROUND OF THE INVENTION

Compounds of structural formula I are known from U.S. Pat. Nos. 4,677,115 and 4,797,413 and known to be topically effective carbonic anhydrase inhibitors useful in the treatment of ocular hypertension. However, the processes described for their preparation result in diastereomeric or racemic products which must be separated and resolved, with concomitant loss of at least 50% of the product, to obtain the most active enantiomer.

The catalyst used in the novel process of this invention is an oxazaborolidine catalyst. Catalysts of this type have been described by Corey et al., *J. Amer. Chem. Soc.* 1987, 109, 7925–7926; *J. Amer. Chem. Soc.* 1987, 109, 5551–5553; *J. Org. Chem.*, 1988, 53, 2861–2863; *Tetrahedron Lett.*, 1989, 30, 5547–5550; *Tetrahedron Lett.*, 1989, 30, 6275–6278; *Tetrahedron Lett.*, 1990, 31, 611–614; Youn et al., *Tetrahedron Lett.*, 1988, 29, 4453–4456; Itsuno, *J. Chem. Soc., Perkin Trans.* 1, 1984, 2887; *J. Chem. Soc., Chem. Comm.*, 1983, 469; and *J. Org. Chem.*, 1984, 49, 555.

Now with the present invention there is provided an enantioselective synthesis which obviates the production of the less active enantiomer and the concomitant loss of material that results from the discarding of that less active enantiomer and the usual material losses encountered in separation of optical isomers and isolation procedures.

DETAILED DESCRIPTION OF THE INVENTION

The novel process of the present invention comprises Step E through Step H of the following reaction scheme:

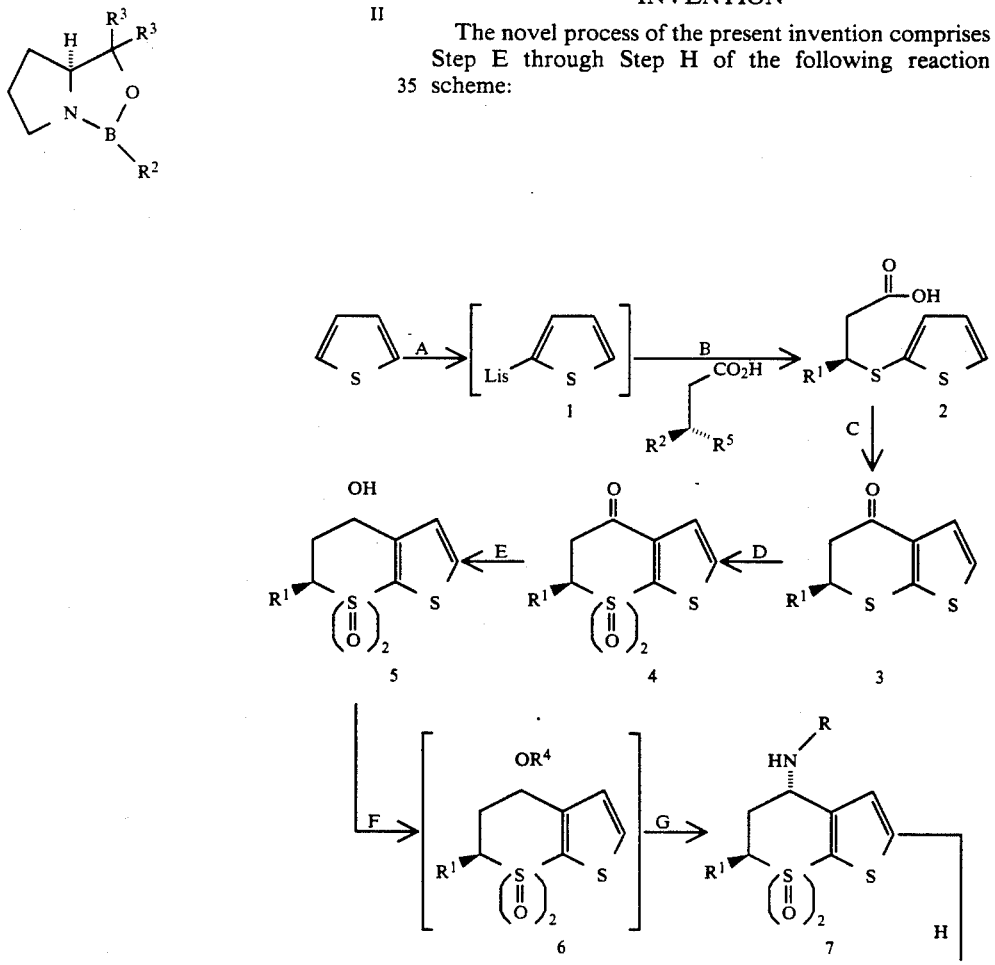

-continued

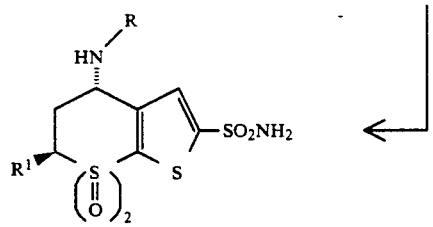

wherein

R is $C_{2-4}$ alkyl;

$R^1$ is hydrogen, $C_{1-3}$ alkyl, or $C_{1-3}$ alkoxy-$C_{1-3}$ alkyl;

R4 is —$SO_2C_{1-4}$alkyl, —$SO_2C_6H_5$, —$SO_2C_6H_4$—$CH_3$, —$SO_2C_6H_4$—Cl, —$SO_2C_6H_4$—Br, —$SO_2C_6H_4$—$OCH_3$ or —$SO_2C_6H_4$—$NO_2$, especially —$SO_2C_6H_4$—$CH_3$ and;

$R^5$ is —$OSO_2C_{1-4}$ alkyl, —$OSO_2C_6H_5$ or —$OSO_2C_6H_4$—$CH_3$, —$OSO_2C_6H_4$—Br, —$OSO_2C_6H_4$—$OCH_3$, —$OSO_2C_6H_4$—$NO_2$, —$OSO_2C_6H_4Cl$, or —Br, especially —$SO_2C_6H_4$—$CH_3$.

The cornerstone of this novel process is the introduction of chirality by an asymmetric reduction (Step E) followed by activation (Step F) and $S_N2$ displacement (Step G). In contrast with the prior art processes, the sulfonamide group is introduced in the present process late in the synthesis as it presents solubility problems and reaction interference during reduction.

The asymmetric reduction is accomplished with a borane reducing agent such as borane-THF complex, diborane or borane-methyl sulfide complex (BMS), preferably the latter, in the presence of an oxazaborolidine catalyst of structural formula:

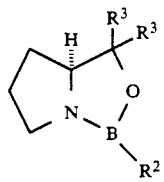

wherein $R^2$ and $R^3$ independently are (a) $C_{1-5}$alkyl, preferably methyl; or (b) phenyl, either unsubstituted or substituted with (1) halo, such as fluoro or chloro, (2) $C_{1-4}$alkyl, preferably methyl, (3) trifluoromethyl, or (4) $C_{1-3}$alkoxy, preferably methoxy.

It is preferred that $R^2$ be methyl or phenyl and that $R^3$ be phenyl.

The reduction process comprises treating the ketone, 4, in a dry ethereal solvent such as THF, ether or 1,2-dimethoxyethane at about −20° to +30° C., especially about −20° to −10° C. with the reducing agent in the presence of the oxazaborolidine catalyst followed by aging the reaction for about 20-60 minutes. The reaction is quenched by cautious addition of a lower alkanol, preferably methanol.

The secondary alcohol product, 5, is isolated by concentration of the above alkanolic solution to a small volume to remove boron species and then separated from diphenylprolinol on an Amberlyst ® 15 (ammonium cycle) column by elution with methanol to obtain the hydroxysulfone, 5.

The diphenylprolinol can be recovered and recycled by elution of the column with methanol/aqueous ammonia mixtures.

The separation of diphenylprolinol from the desired hydroxysulfone, 5, by retention on the Amberlyst ® 15 resin and subsequent removal with methanol/ammonia without racemization is novel and quite unexpected and forms another embodiment of this invention.

The intermediate sulfonyloxy compound, 6, cannot be formed satisfactorily by the usual procedure of treatment with toluenesulfonyl chloride and pyridine or other tertiary amine, inasmuch as considerable displacement of hydroxy with chloride occurs. Stoichiometric deprotonation of the alcohol with an organo-lithium or sodium compound such as n-butylithium, sodium bis(-trimethylsilyl)amide or sodium acetylide followed by treatment with an alkyl or aryl sulfonic anhydride or chloride such as toluenesulfonic anhydride or toluenesulfonyl chloride, especially the latter, has proved to provide the best yield and enantiomeric purity. In practice, the hydroxysulfone in an ethereal solvent such as THF, diethyl ether, or dimethoxyethane at about 10°-20° C. is treated with a stoichiometric amount of sodium acetylide over a period of about 5 to 15 minutes followed by aging for about an hour. Then at about −20° to −5° C., toluenesulfonyl chloride in an ethereal solvent is added at a rate sufficient to maintain a temperature of about −15° to −5° C. and the reaction is aged about 1 to 2 hours.

The displacement with the amine, $RNH_2$, is accomplished by adding an excess of the amine to the solution of the tosyl compound 6 and aging the reaction mixture for about 10 to 20 hours. The product 7 is isolated by acidification and concentration to remove organic solvents followed by basification and extraction.

Introduction of the sulfonamide group required forcing conditions and is best accomplished with fuming sulfuric acid at about 5° to 10° C. over about 1-3 hours followed by addition of excess thionyl chloride and refluxing for about 1-3 hours followed by evaporation of excess thionyl chloride.

The reaction is cautiously quenched by addition of the sulfuric acid solution to concentrated aqueous ammonia/THF 1:1(v:v) at about −25° to −15° C. at a rate sufficient to maintain the temperature below about 0° C. and stirring about one hour after the addition is complete.

EXAMPLE

S-(+)-5,6-Dihydro-4-(2-methylpropyl)amino-4H-thieno[2,3-b]thiopyran-2-sulfonamide-7,7-dioxide

Steps A and B

Preparation of 3-(2-thienylthio)propanoic acid (2)

In a 2-L, three-necked round-bottomed flask fitted with a thermometer, nitrogen inlet, mechanical stirrer and addition funnel was placed thiophene (64 mL, 799 mmol;) and sieve dried THF (400 mL, residual water ≦120 μg/mL). The solution was cooled to 0°-5° C. and 1.6M n-butyllithium (470 mL, 751 mmol) was added at such a rate as to maintain the temperature at <20° C. The reaction was stirred for 1 hour at 0°-5° C., and was used immediately in the next sequence. To the cooled reaction mixture (0°-5° C.) was added sulfur (24 g, 750 mmol) portionwise while maintaining the temperature at <20° C. The reaction was stirred for an additional 2.0 hour at 0°-5° C. after which nitrogen-purged water (300 mL) was added at such a rate as to maintain the temperature at <18° C. The addition of sulfur was highly exothermic. (Note: The 2-mercaptothiophene and its anion (1) can air-oxidize to the corresponding disulfide. Therefore, solutions of 1 must be deoxygenated and stored under a nitrogen atmosphere). Solids may form initially upon addition of water to the solution of 1 but eventually dissolve. The solution of 1 was titrated for total base. The yield of thiophene to 1 based on titration was 98%.

In a 1-L, 3-necked, round-bottomed flask fitted with an addition funnel, thermometer, nitrogen sweep and mechanical overhead stirrer was prepared a solution of potassium carbonate (46.5 g, 337 mmol) in nitrogen-purged water (85 mL). To this solution was added solid 3-bromopropionic acid (116 g, 736 mmol) at such a rate as to control foaming ($CO_2$ evolution). The mixture was stirred until a clear solution was obtained. The temperature increased from 23° C. to 50° C. during the dissolution of potassium carbonate. (Note: Foaming occurs during the addition of 3-bromopropionic acid to the potassium carbonate solution with the evolution of carbon dioxide). The solution was cooled to 10° C. and the aqueous solution of potassium 3-bromopropionate was added at such a rate as to maintain the temperature at 0°-5° C. The reaction was stirred for 24 hours at ambient temperature. The layers were separated and the aqueous layer was washed twice with toluene (100 mL portions) to remove neutral organic impurities. The aqueous layer was then cooled to 10° C. and stirred with toluene (300 mL) as aqueous HCl (125 mL, 6N) was added, maintaining the temperature at <14° C. (pH<1). The organic layer was separated and the aqueous layer extracted with additional toluene (300 mL). The organic layers were combined and dried azeotropically under vacuum to a volume of 500 mL and residual water of ≦2.5 mg/mL. The solution was stored at 0°-5° C. overnight. A small amount of the carboxylic acid was isolated and characterized as its tert-butylammomium salt: m.p. 110°-112° C. Anal. Calcd for $C_{11}H_{19}NO_2S_2$: C, 50.54; H, 7.33; N, 5.36. Found: C, 50.53; H, 7.12; N, 5.27.

Step C

Preparation of
5,6-dihydro-4H-thieno[2,3-b]thiopyran-4-one (3)

In a 2-L reactor fitted with an overhead mechanical stirrer, thermometer, addition funnel, reflux condenser, and nitrogen bubbler vented through an acid-vapor scrubber was placed the toluene solution of 2 (130.7 g, 695 mmol). The reaction mixture was brought to an initial temperature of 20° C. and trifluoroacetic anhydride (161 g, 765 mmol) was added over 5 minutes to the stirred solution of 2. The reaction was then heated to 35°-38° C. and stirred for about 1.5 hours. The reaction mixture was then slowly added to water (500 mL) maintaining the temperature at <25° C. A pH probe was placed in the vessel and the mixture was titrated to pH 7.0 with 50% sodium hydroxide (123 g, 1.53 mole). The layers were separated and the aqueous phase was extracted once with toluene (200 mL), The combined organic extracts were then concentrated under vacuum (43 mBar) to a volume of 200 mL and then diluted to 1.2 L with ethyl acetate for the next step (oxidation). A small sample was chromatographed to obtain the following data: $R_f=0.29$ (85:15 hexane:ethyl acetate). m.p. 61°-62° C. $^1H$ NMR: δ7.42 (d, J=5.4, H$_2$); 6.98 (d, J=5.4 H$_3$); 3.33 (m, C$_5$H$_2$); 2.82 (m, C$_6$H$_2$). $^{13}C$ NMR; $δ_c$ 188.9 (C$_4$), 150.9, 135.0 (C$_{3a}$, C$_{7a}$), 126.1, 121.8 (C$_2$, C$_3$), 38.1 (C$_6$), 30.0 (C$_5$). Anal Calcd for $C_7H_6OS_2$: C, 49.39; H, 3.55; S, 37.66. Found: C, 49.56; H, 3.58; S, 37.68.

Step D

Preparation of
5,6-dihydro-4H-thieno[2,3-b]thiopyran-4-one-7,7-dioxide (4)

The ethyl acetate/toluene solution of ketone 3 (118 g, 765 mmol in 1.2 L of 5:1 v:v ethyl acetate/toluene) was charged to a 5-L three-necked round-bottomed flask equipped with an overhead mechanical stirrer, 250-mL pressure-equalizing dropping funnel, and thermocouple temperature probe. The mixture was stirred and water (35 mL) was added to saturate the organic phase. A solution of sodium tungstate dihydrate (11.7 g, 77 mmol) dissolved in water (35 mL) was then added (caution: there is an induction period of several minutes before an exotherm). The mixture was heated to 35° C. and hydrogen peroxide (30%, 250 mL, 2.43 mole) was added over 45 minutes. The temperature of the reaction was allowed to rise to 55°-58° C. until judged complete by HPLC: 4.1×254 mm Altex C-8, 5-micron ultrasphere column at 45° C. (2 mL/min, gradient from 65:35 to 20:80 0.1% $H_3PO_4$ in $H_2O$: $CH_3CN$ over 20 minutes, then isocratic for 5 minutes 230 nm) $R_1$ (sulfoxide) 6.9 minutes, (sulfone) 10.6 minutes, (sulfide) 15.8 minutes. On completion the mixture was cooled to 0°-5° C. and excess hydrogen peroxide was decomposed by the slow addition of aqueous sodium sulfite (205 g, 1.63 mole dissolved in 700 mL water). The temperature of the reaction mixture was maintained at <20° C. When the reaction mixture tested negative for peroxides with acidified starch-iodide paper, the layers were separated. The upper organic layer was concentrated under vacuum at 45° C. bath temperature to a volume of 400 mL. Hexanes (400 mL) were then added over approximately 10 minutes and the batch was aged for one hour. The product was filtered, washed with hexanes, and dried under vacuum at 60° C. with a nitrogen sweep to constant weight. The yield of crude ketosulfone 4 was 113 g (76% from 3-bromopropionic acid). Crude ketosulfone was then recrystallized from methanol in the following procedure. A quantity of 113 g crude ketosulfone was dissolved in 3 L of anhydrous methanol at 55°-60° C. The solution was cooled to 40° C. and 10 g of Calgon ADP ® carbon was added. The mixture was aged at 40° C. for a minimum of 4 hours. The batch was then filtered warm at 40° C. through a well-washed pad of SuperCel ®. The filter cake was washed with two 500 mL portions of methanol at 40° C. and filtrates were combined. The batch was then concentrated under vacuum to a volume of 500 mL and aged at 0°-5° C. for 4 hours. Crystallization ensued during concentration. The batch was filtered, washed with 75 mL cold methanol, sucked dry under nitrogen, and dried under vacuum (25" Hg) at 80° C. with a nitrogen sweep for 12 hours. The recovery yield was 100 g (89%) assayed @

99.6 wt % by HPLC against an external standard. $R_f = 0.30$ (dichloromethane). m.p. 121°–121.5° C. $^1$H NMR: δ 7.60 (d, J=5.1, H$_2$); 7.50 (d, J=5.1, H$_3$); 3.76 (m, C$_5$H$_2$); 3.36 (m, C$_6$H$_2$). $^{13}$C NMR: δ$_c$ 186.3 (C$_4$), 147.2 (C$_{3a}$), 139.3 (C$_{7a}$), 130.2 (C$_2$), 126.3 (C$_3$), 52.8 (C$_6$), 37.0 (C$_5$). MS (EI, 70 eV): 202 (M+,35), 174 (38), 138 (15), 110 (100), 84 (30), 82 (25), Anal Calcd for C$_7$H$_6$O$_3$S$_2$: C, 41.57; H, 2.99; S, 31.70. Found: C, 41.49; H, 3.02; S, 31.60.

Step E

Preparation of
[4]-5,6-dihydro-4H-thieno[2 3-b]thiopyran-4-ol-7,7-dioxide (5)

Ketosulfone 4 (50.0 g, 0.247 moles) was dissolved in tetrahydrofuran (700 mL) over 4 Å molecular sieves (20 g) and occasionally swirled until the residual water content was <40 μg/mL (~2 h). A 2-L three-necked flask fitted with a mechanical stirrer, nitrogen inlet tube, 500-mL addition funnel and teflon coated thermocouple probe, was charged with 4 (decanted from the sieves). To the solution was added oxazaborolidine catalyst (R$^2$=CH$_3$, R$^3$=C$_6$H$_5$) (14.4 mL of a 0.86M solution in toluene). The resulting solution was cooled to −15° C. In a separate vessel borane-methyl sulfide (17.3 mL) was dissolved in dry tetrahydrofuran (297 mL; residual water <40 μg/mL). The borane-methyl sulfide solution was placed in the addition funnel and added to the ketosulfone/catalyst solution at a rate to maintain an internal temperature at −15° C. (~30 minutes). After all of the borane was added, the reaction was aged for 30 minutes. An easily stirred precipitate usually formed during the age. The reaction was quenched by the cautious addition of 10 mL of methanol (Caution: There was a significant induction period (1-2 minutes) before hydrogen was evolved after the initial methanol was added) maintaining the temperature at 10° C. After hydrogen evolution subsided, the remaining methanol (365 mL) was added. The reaction became homogeneous during the quench. After complete addition of methanol, the reaction mixture was warmed to 20° C. and stirred for 12 hours. The resulting solution was concentrated at atmospheric pressure to approximately 125 mL. Methanol (375 mL) was added and the resulting solution was concentrated at atmospheric pressure to 125 mL to remove any remaining boron species.

Amberlyst ® 15 (56 g, 100 mL dry) was suspended in methanol (100 mL). (Caution: The slurry exotherms to approximately 40° C. without external cooling and expands on wetting to approximately 1.5 times its initial volume). The slurry was poured into a 2.5×30 cm column and eluted with 1 L of ammonium hydroxide (15M) in methanol (6 vol %, ~1M) until the eluate was basic (pH~11 when diluted 1:1 with water). The initial brown eluate was discarded. The column was eluted with methanol (~500 mL) until the eluate was neutral. The methanol solution of (R)-hydroxysulfone (~50 g) and (S)-diphenylprolinol (3.13 g) was filtered through a pad of SuperCel. ® The cake was washed with methanol (2×50 mL) and the combined filtrates brought to a volume of 500 mL (10 mL/g) with methanol. The filtered methanol solution was eluted through the column containing Amberlyst ® 15 (NH$_4$+) at 3.8 mL/min collecting 38 mL fractions. The column was rinsed with methanol (380 mL) to remove all of the product hydroxysulfone. The column was then eluted with 94:6 (v/v) methanol/15M aqueous ammonia (400 mL) to elute diphenylprolinol. Fractions 3-21 containing (R)-hydroxysulfone (95:5 R:S, 49 g (98%), contaminated with less than 0.4% diphenylprolinol) were combined and concentrated (recrystallization of this material from hexanes/ethyl acetate only serves to lower enantiomeric purity).

A small sample was chromatographed to obtain characterization data: $R_f = 0.07$ (60:40 hexane:ethyl acetate). [α]D$^{21}$ = +16.4 (c 0.210, MeOH). m.p. 89°–90° C. IR (CHCl$_3$): 3600 w (OH), 3550–3400 br w (OH), 3110 w, 3010 m, 2940 w, 1520 w, 1400 m, 1305 s (SO$_2$), 1285 s, 1180 w, 1145 s (SO2), 1125 s, 1100 w, 1160 m, 1140 m, 970 w, 915 w, 890 w, 845 w, 825 m. $^1$H NMR: δ 7.59 (d, J=5.1, H$_2$), 7.12 (d, J=5.1, H$_3$), 4.91 (ddd, J=10.0, 5.9, 1.5, H$_4$), 3.62 (m, H$_6$), 3.31 (m, H$_6$), 2.75 (m, H$_5$), 2.55 (m, H$_5$, OH). $^{13}$C NMR: δ$_c$ 144.9 (C$_{3a}$), 135.9 (C$_{7a}$), 130.5 (C$_2$), 127.0 (C$_3$), 63.5 (C$_4$), 49.1 (C$_6$), 31.0 (C$_5$). Anal Calcd for C$_7$H$_8$O$_3$S$_2$: C, 41.16; H, 3.95; S, 31.39. Found: C, 41.23; H, 3.93; S, 31.24.

Steps F and G

Preparation of
(S)-5,6-dihydro-N-(2-methylpropyl)-4H-thieno[2,3-b]thiopyran-4-amine-7,7-dioxide (7)

A 3-L three-neck flask fittered with a mechanical stirrer, nitrogen inlet tube, 500-mL addition funnel and teflon coated thermocouple probe, was charged with hydroxysulfone 5 (50.0 g, 0.245 moles) dissolved in dry tetrahydrofuran (500 mL). The solution was cooled to 15° C. A slurry of sodium acetylide in xylene/light mineral oil (12-9 g, 0.270 mmol of an 18% slurry) was well mixed with 400 mL of tetrahydrofuran and added to the hydroxysulfone over 5 minutes. The resulting suspension was stirred at 20° C. for 90 minutes. During the age, the fine slurry of sodium acetylide was converted to the easily stirred, coarse, crystalline sodium salt of the hydroxysulfone. The resulting slurry was cooled to −15° C. Toluenesulfonyl chloride (51.3 g, 0.269 mol) was dissolved in 250 mL of tetrahydrofuran and placed in the addition funnel. The toluenesufonyl chloride/tetrahydrofuran solution was added to the sodium salt at a rate to maintain the internal temperature below −10° C. for 2 hours. The tosylation can be followed by TLC on silica with hexanes/ethylacetate (6:4); alcohol $R_f = 0.07$; tosylate $R_f = 0.37$. The sodium salt of the hydroxysulfone dissolved during the age and the reaction usually turned dark green. (Note: tosylate 6 should not be isolated since it readily hydrolyzes to racemic 5 in water). Dry (residual water <100 μg/mL) isobutylamine (250 g, 340 mL, 3.43 mol) was added over 5 minutes. The resulting mixture was warmed to 20° C. and aged for 14 hours. (This reaction was monitored by TLC analysis: 60:40 hexane:ethyl acetate; $R_f$. tosylate 6, 0.37, amine 70.25). The resulting mixture was cooled to −15° C. and aqueous hydrochloric acid (1.54 L, 2N) was added at a rate to maintain the internal temperature at or below 5° C. (approximately 30 minutes). The resulting pH was approximately 2.5. The solution was concentrated to approximately 1.6 L to remove most (90%) of the tetrahydrofuran and extracted twice with 1 L of isopropyl acetate. The aqueous phase was cooled to 0° C. and sodium hydroxide (120 mL, 5N) was added at a rate to maintain the internal temperature below 5° C. (approximately 5 minutes). The resulting pH was approximately 9.5 and the reaction mixture became cloudy upon addition of sodium hydroxide. The resulting mixture was extracted twice with isopropyl acetate (1 L). The organic layers were combined and concentrated to approximately 120 mL. Isopropanol (600 mL) was added and the mixture was concentrated to 100 mL. A second flush was performed to remove the isopropyl acetate. Isopropanol was added to bring the volume to approximately 1 L and the resulting solution was warmed to 55°-60° C. and Calgon ADP® (5 g) decolorizing carbon was added. The mixture was stirred at 50° C. for 4 hours. The resulting mixture was filtered (at 50° C.) through prewashed SuperCel®. The filtered solution was concentrated to 0.86 L (14 mL/g amine) and allowed to cool slowly to room temperature. The resulting suspension was cooled to 0° C. and aged for 2 hours. The suspension was filtered, washed twice with 150 mL of 0° C. isopropanol and dried in vacuo at 45° C. for 12 hours to yield 47 g (73%) of amine 7 (R=2-methylpropyl) as off white crystals.

Data for 7: $R_f=0.25$ (60:40 hexane:ethyl acetate). $[\alpha]_D^{22}=-8.68$ (c 0.316, MeOH). m.p. 86°-86.5° C. $^1$H NMR: $\delta$7.53 (d, J=5.0, H$_2$), 7.08 (d, J=5.0, H$_3$), 3.91 (dd, J=6.3, 4.1, H$_4$), 3.68 (ddd, J=13.6, 9.8, 2.8 H$_6$), 3.27 (ddd, J=9.3, 8.8, 2.6, H$_{6'}$,), 2.55 (m, C$_5$H$_2$,C$_1$,H$_2$), 1.68 (nine lines, J= 6.6), 0.92 (d, J=6.8). $^{13}$C NMR; $\delta$c 146.0 (C$_{3a}$), 135.6 (C$_{7a}$), 129.7 (C$_2$), 127.1 (C$_3$), 55.0 (C$_1$,), 52.6 (C$_4$), 49.6 (C$_6$), 28.8 (C$_2$,), 27.8 (C$_5$), 20.6, 20.5 (2×CH$_3$). Anal Calcd for C$_{11}$H$_{17}$NO$_2$S$_2$: C 50.94; H, 6.64; N, 5.40; S. 24.72. Found: C, 51.00; H, 6,64; N, 5,30; S, 24.50. Enantiomeric purity >99:1.

Step H

Preparation of (S)-(+)-5,6-Dihydro-4-(2-methylpropyl)amino)-4H-thieno[2,3-b]-thiopyran-2-sulfonamide-7,7-dioxide monohydrochloride hemihydrate (8)

A 1 L round bottom flask fitted with a mechanical stirrer, nitrogen inlet and septum was charged with fuming sulfuric acid (12-20% SO$_3$ in H$_2$SO$_4$, 125 mL). Caution: Fuming sulfuric acid (oleum) is extremely corrosive. The solution was cooled to $-15°$ C. and amine 7 (25 g, 96.4 mmol) was added in five portions over 1 hour. Caution: The addition is exothermic. After stirring the resultant solution for 2 hours at 5°-8° C., thionyl chloride (375 mL, 611 g, 5.14 mol) was added and the mixture was refluxed for 3 hours. The thionyl chloride was removed by distillation and the resulting oil was cooled to 0° C. A 5-L round bottomed flask fitted with a mechanical stirrer, 250-mL pressure equalizing addition funnel (with a teflon tube attached to the bottom that reached below the surface of the contained liquid) and nitrogen inlet was charged with 800 mL of concentrated aqueous ammonia and 800 mL of tetrahydrofuran and cooled to 0° C. The addition funnel was charged with the sulfuric acid solution of the sulfonyl chloride. The sulfuric acid solution was slowly added to the ammonia at a rate to maintain the temperature below 0° C. (~1 hour). Caution: Addition of strong acid to strong base is exothermic and spattering may occur. After complete addition, the resulting mixture was stirred at 0° C. for 30 minutes. The resulting pH was 10. The resulting suspension was filtered and the filter cake washed with 2×600 mL of tetrahydrofuran. The filtrate was concentrated to remove tetrahydrofuran and extracted with 2×600 mL of ethyl acetate. The organic layers were combined, concentrated to 375 mL and stirred well as concentrated hydrochloric acid (12 mL, 145 mmol) was slowly added. The mixture was concentrated under vacuum at 45° C. (bath temperature) to remove water, replacing ethyl acetate as necessary, until a solution with a water content of <0.1 mg/mL was attained at a volume of approximately 350 mL. The crystallized mixture was allowed to cool and stirred at ambient temperature overnight. The slurry was filtered and washed with two bed volumes of ethyl acetate. The white solid was dried under vacuum at 45° C. to afford 26 g of product·HCl. The salt could be recrystallized from water as follows. The salt (25 g, 73 mmol) was dissolved in water (50 mL) at 90° C. The mixture was well stirred and activated carbon (Darco KB®, 2.5 g) was added to the hot mixture.

After stirring for 2 hours, the mixture was filtered hot (85°-90° C.) through a washed bed of SuperCel® and the filter cake washed with 10 mL of boiling water. The combined filtrate and wash was allowed to slowly cool to 50°-60° C. and held at 50°-60° C. until crystallization occurred. After stirring for 1 hour at 60° C. after crystallization occurred, the mixture was cooled to 3° C. and aged for 1 hour. The resulting mixture was filtered and the filter cake washed with cold water (10 mL). The product was dried under vacuum at 45° C. with a nitrogen sweep to afford 21 g (71%) of product·HCl. $[\alpha]_D^{25}=+49°$ (c=0.50, MeOH).

m.p. 222d° C. IR (KBr): 3350 w (NH), 2950 s, 2800-2300 w (NH$_2$+), 1620 w, 1590 w, 1540 m, 1466 w, 1420 w, 1400 w, 1350 s (SO$_2$), 1340 s (SO$_2$), 1300 s (SO$_2$), 1160 s (SO$_2$), 1145 s (SO$_2$), 1050 m, 1020 m, 910 w, 880 m, 740 m, 700 w. $^1$H NMR (DMSO-d$_6$): $\delta$ 9.82 (br s, C$_4$NH$_2$+), 8.20 (s, SO$_2$NH$_2$), 8.16 (s, C$_3$H), 4.80 (br s, C$_4$H), 3.94 (m, C$_6$H$_2$), 3.83 (s, H$_2$O), 2.82 (m, C$_5$H$_2$, C$_1$'H$_2$), 2.15 (septet, J=6.6, C$_2$'H), 0.98 (d, J=6.6, CH$_3$), 0.96 (d, J=6.6, CH$_3$). $^{13}$C NMR (DMSO-d$_6$): $\delta$c 149.4 (C$_2$), 141.8 (C$_{7a}$), 137.5 (C$_{3a}$), 129.8 (C$_3$), 51.2 (C$_6$), 50.9 (C$_4$), 48.3 (C$_1$'), 25.5 (C$_2$'), 23.7 (C$_5$), 20.3, 20.0 (2×CH$_3$). HRMS (free base, EI, 90 eV) Calcd for C$_{11}$H$_{18}$N$_2$O$_4$S$_2$: 338.0429. Found: 338.0430. Anal. Calcd for C$_{11}$H$_{19}$ClN$_2$O$_4$S$_3$·0.5 H$_2$O: C, 34.41; H, 5.25; N, 7.30; S, 25.05; Cl, 9.23. Found: C, 35:55; H, 5.20; N, 7.21; S, 24.89; Cl, 9.50.

Employing the procedures substantially as described in the foregoing Example 1, but substituting for the isobutylamine used in Steps F and G, an equivalent amount of an amine of structure RNH$_2$ and a 6-R$^1$-hydroxysulfone shown in Table I, there are prepared the S-5,6-dihydro-6-R$^1$-4-R-amino-4H-thieno[2,3-b]thiopyran-2-sulfonamide-7,7-dioxides also shown in Table I:

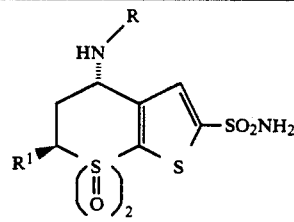

| R | R$^1$ |
|---|---|
| C$_2$H$_5$— | CH$_3$— |
| C$_2$H$_5$— | C$_2$H$_5$— |
| n-C$_3$H$_7$— | CH$_3$ |
| n-C$_4$H$_9$— | CH$_3$ |
| i-C$_3$H$_7$ | n-C$_3$H$_7$ |
| C$_2$H$_5$— | CH$_3$OCH$_2$CH$_2$— |
| C$_2$H$_5$— | CH$_3$CH$_2$OCH$_2$CH$_2$— |
| C$_2$H$_5$— | CH$_3$CH$_2$O(CH$_2$)$_3$— |
| C$_2$H$_5$ | CH$_3$O(CH$_2$)$_4$— |
| C$_2$H$_5$ | C$_4$H$_9$O(CH$_2$)$_2$— |

-continued

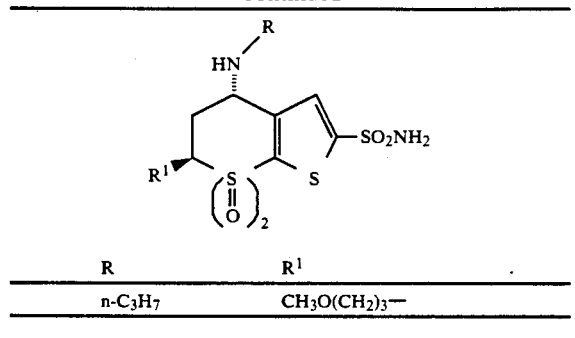

| R | R¹ |
|---|---|
| n-C₃H₇ | CH₃O(CH₂)₃— |

EXAMPLE 2

Effect of Substitution on the Oxazaborolidine Catalyzed Borane Reduction

The effect of the substitution on the oxazaborolidine catalyst on the enantiomeric purity of the hydroxysulfone, 5, is shown in the following table:

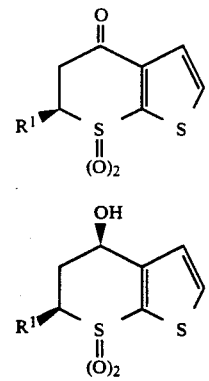

| $R^2$ | $R^3$ | (R):(S) |
|---|---|---|
| —CH₃ | C₆H₅— | 98:2 |
| CH₃ | 4-F—C₆H₄— | 97:3 |
| —CH₃ | 4-Cl—C₆H₄— | 97:3 |
| —CH₃ | 4-CH₃—C₆H₄— | 96:4 |
| —CH₃ | 4-CF₃—C₆H₄— | 98:2 |
| —CH₃ | 4-t-Bu—C₆H₄— | 95:5 |
| —CH₃ | 4-CH₃OC₆H₄— | 93:7 |
| -n-C₄H₉ | C₆H₅— | 93:7 |
| —C₆H₅ | C₆H₅— | 96:4 |
| 4-F—C₆H₄— | C₆H₅— | 99:1 |
| 4-Cl—C₆H₄— | C₆H₅— | 98:2 |
| 4-CH₃—C₆H₄— | C₆H₅— | 99:1 |
| 4-CF₃—C₆H₄— | C₆H₅— | 98:2 |
| 4-CH₃OC₆H₄— | C₆H₅— | 97:3 |

What is claimed is:

1. A process for the preparation of a compound of structural formula 8

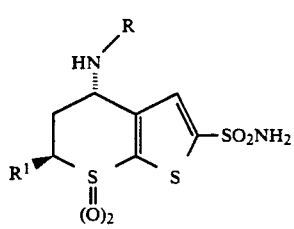

or an ophthalmologically acceptable salt thereof wherein

R is $C_{1-4}$ alkyl; and $R^1$ is hydrogen, $C_{1-4}$ alkyl or $C_{1-4}$ alkoxy-$C_{1-4}$ alkyl which comprises the steps of:

a) asymmetric reduction of a compound of structural formula 4 to a compound of structural formula 5

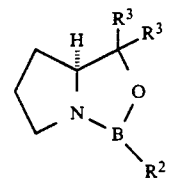

with a borane reducing agent in the presence of an oxazaborolidine catalyst of structural formula:

wherein $R^2$ and $R^3$ independently are
1) $C_{1-5}$ alkyl,
2) phenyl, either unsubstituted or substituted with one or more of
   i) halo,
   ii) $C_{1-4}$ alkyl,
   iii) $CF_3$, or
   iv) $C_{1-3}$ alkoxy;

b) treatment of compound 5 with an organolithium or organosodium compound and $C_{1-4}$alkyl- or arylsulfonyl chloride or anhydride to form the compound of structural formula 6

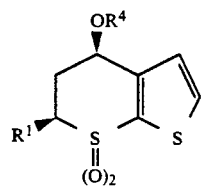

wherein $R^4$ is —SO₂C₁₋₄alkyl, —SO₂C₆H₅, —SO₂C₆H₄—CH₃, —SO₂C₆H₄—OCH₃, —SO₂C₆H₄—Br, —SO₂C₆H₄—Cl or —SO₂C₆H₄—NO₂;

c) treatment of compound 6 with an amine of formula R-NH₂ to form the compound of structural formula 7; and

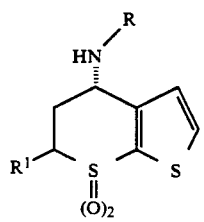

d) treatment of compound 7, with fuming sulfuric acid, chlorosulfonic acid and aqueous ammonia in series to form the compound of structural formula 8.

2. The process of claim 1, for preparation of the compounds wherein R is isobutyl and $R^1$ is hydrogen; R is ethyl and $R^1$ is methyl; and R is n-propyl and $R^1$ is $CH_3O(CH_2)_3$.

3. The process of claim 1, wherein $R^2$ is —$CH_3$ and $R^3$ is phenyl.

4. The process of claim 2, wherein $R^2$ is —$CH_3$ and $R^3$ is phenyl.

5. The process of claim 1, wherein $R^4$ is 4—$CH_3$—$C_6H_4SO_2$—.

6. The process of claim 2, wherein $R^4$ is 4—$CH_3$—$C_6H_4SO_2$—.

7. The process of claim 3, wherein $R^4$ is 4—$CH_3$—$C_6H_4SO_2$—.

8. The process of claim 4, wherein $R^4$ is 4—$CH_3$—$C_6H_4SO_2$—.

9. The process for the preparation of compound 7:

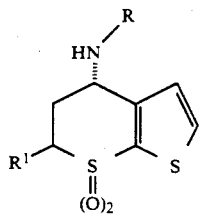

comprising steps (a), (b) and (c) of claim 1.

10. The process of claim 9 for preparation of the compound wherein R is isobutyl and $R^1$ is hydrogen; R is ethyl and $R^1$ is methyl; and R is n-propyl and $R^1$ is $CH_3O(CH_2)_3$—.

11. The process of claim 9 wherein $R^2$ is —$CH_3$ and $R^3$ is phenyl.

12. The process of claim 10 wherein $R^2$ is —$CH_3$ and $R^3$ is phenyl.

13. The process of claim 9 wherein $R^4$ is 4—$CH_3$—$C_6H_4SO_2$—.

14. The process of claim 10 wherein $R^4$ is 4—$CH_3$—$C_6H_4SO_2$—.

15. The process of claim 11 wherein $R^4$ is 4—$CH_3$—$C_6H_4SO_2$—.

16. The process of claim 12 wherein $R^4$ is 4—$CH_3$—$C_6H_4SO_2$—.

17. The process for the preparation of compound 6

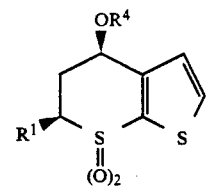

comprising steps (a) and (b) of claim 1.

18. The process of claim 17 wherein $R^1$ is hydrogen, methyl or $CH_3O(CH_2)_3$—.

19. The process of claim 17, wherein $R^2$ is —$CH_3$ and $R^3$ is —$C_6H_5$.

20. The process of claim 18, wherein $R^2$ is —$CH_3$ and $R^3$ is —$C_6H_5$.

21. The process of claim 17 wherein $R^4$ is 4—$CH_3$—$C_6H_4SO_2$—.

22. The process of claim 18 wherein $R^4$ is 4—$CH_3$—$C_6H_4SO_2$—.

23. The process of claim 19 wherein $R^4$ is 4—$CH_3$—$C_6H_4SO_2$—.

24. The process of claim 20 wherein $R^4$ is 4—$CH_3$—$C_6H_4SO_2$—.

25. The process for the preparation of the compound 5

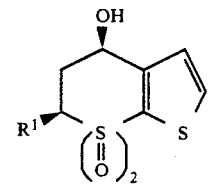

comprising step (a) of claim 1.

26. The process of claim 25 wherein $R^2$ is —$CH_3$ and $R^3$ is phenyl.

27. The process of claim 25 wherein $R^1$ is hydrogen, methyl or $CH_3O(CH_2)_3$—.

28. The process of claim 26 wherein $R^1$ is hydrogen, methyl or $CH_3O(CH_2)_3$—.

* * * * *